United States Patent [19]

Brown et al.

[11] 4,376,819

[45] Mar. 15, 1983

[54] BIOLOGICAL EXTRACTS AND METHOD FOR MAKING SAME

[75] Inventors: R. Clark Brown, Round Lake Beach; Richard Cotter, Libertyville; Susan K. Young, North Chicago, all of Ill.

[73] Assignee: Baxter Travenol Laboratories, Inc., Deerfield, Ill.

[21] Appl. No.: 236,963

[22] Filed: Feb. 23, 1981

Related U.S. Application Data

[63] Continuation-in-part of Ser. No. 75,579, Sep. 14, 1979, abandoned.

[51] Int. Cl.³ ............... C12Q 1/00; C12Q 1/36; C12Q 1/38
[52] U.S. Cl. .................................. 435/4; 435/7; 435/23; 435/24; 435/29; 435/184; 435/212; 435/219; 435/226; 436/502
[58] Field of Search ............ 23/230 B; 252/408 R; 424/2, 94; 435/23, 24, 184, 212, 219, 226, 4, 7, 29

[56] References Cited

U.S. PATENT DOCUMENTS

| | | | |
|---|---|---|---|
| 3,915,805 | 10/1975 | Levin | 424/2 |
| 3,944,391 | 3/1976 | Harris et al. | 23/230 B |
| 3,954,663 | 5/1976 | Yamamoto et al. | 424/2 |
| 4,024,285 | 5/1977 | Beuk et al. | 435/184 |
| 4,038,029 | 7/1977 | Teller et al. | 435/23 |
| 4,038,147 | 7/1977 | Reno | 435/23 |
| 4,096,091 | 6/1978 | Hopkins | 435/24 |
| 4,104,030 | 8/1978 | Hopkins et al. | 435/34 |
| 4,107,077 | 8/1978 | Sullivan et al. | 435/34 |
| 4,221,865 | 9/1980 | Dubczak et al. | 435/34 |

FOREIGN PATENT DOCUMENTS

1499846  2/1978  United Kingdom .

OTHER PUBLICATIONS

Solum, *Thrombosis Research,* 2, 1973, pp. 55–70.
Gaffin, *Biorheology,* 13, 1976, pp. 273–280.
Nachum et al., *J. Invertebrate Pathology,* 32, 1978, pp. 51–58.
Levin et al., *J. Lab. Clin. Med.,* 75 (6), 1976, pp. 903–911.
Wildfeuer et al., *Appl. Micro.,* 28 (5), 1974, pp. 867–871.
"Limulus Amebocyte Lysate for in Process Endotoxin Detection", *Mallinckrodt, Inc.,* 12/72, pp. 1–3.
Mills, "Limulus Amebocyte Lysate for Detection of Endotoxins", *Mallinckrodt Inc.,* 1978, pp. 1–32.
Reinhold et al., "A Technique for Quantitative Measurement of Endotoxin in Human Plasma", *Soc. for Exp. Bio. Med.,* May 1971, p. 334.
Sullivan et al., *Appl. Micro.,* 28 (6), 1974, pp. 1023–1026.
Hochstein et al., *Bulletin of the Parental Drug Assoc.,* 27 (3), 1973, pp. 139–148.
Levin, *New England J. Med.,* 288 (24), 1973, pp. 1297–1298.

*Primary Examiner*—Peter A. Hruskoci
*Attorney, Agent, or Firm*—Paul C. Flattery; Lawrence W. Flynn; Max D. Hensley

[57] ABSTRACT

A p-nitrophenyl hydrolase contaminant present in Limulus coagulase sources interferes in, i.e., inhibits, coagulase-based assays for endotoxin. The contaminant inhibitor enzyme may be removed from coagulase by physical separation or by selective denaturation, for example by adjusting the pH of a coagulase solution to about from 8.5 to 11. Inhibitor-free coagulase is a novel composition. The coagulase activity of the composition is adjusted to a predetermined level to provide a standardized coagulase reagent for use in endotoxin assays.

8 Claims, No Drawings

BIOLOGICAL EXTRACTS AND METHOD FOR MAKING SAME

This application is a continuation-in-part of Ser. No. 75,579, Sept. 14, 1979, now abandoned.

BACKGROUND OF THE INVENTION

This invention relates to the preparation of extracts from the blood cells of organisms such as *Limulus polyphemus*, the horseshoe crab. In particular this invention relates to an improved process for eliminating the variation in performance among various lots of Limulus amebocyte lysates in endotoxin assays.

Coagulase is a proteolytic enzyme, the activity of which is modulated by endotoxin, i.e., the enzyme is allosterically activated by endotoxin. It is not proteolytically active in the absence of endotoxin. Coagulase is known to be found in, and is obtained from the blood amebocytes of *Limulus polyphemus* and *Tachypleus tridentatus*.

Coagulase is usually isolated from the amebocytes by lysing the cells to free the water soluble intracellular components and centrifuged to remove suspended detritus. A suitable technique for obtaining such extracts from Limulus is disclosed in United Kingdom Pat. No. 1,499,846. Such cell-free amebocyte isolates are referred to herein as amebocyte extracts.

The amebocyte extracts are known to contain coagulase and coagulogen. Coagulogen is a protein which is hydrolyzed by activated coagulase to form protein fragments. These fragments are thought to then spontaneously polymerize to yield a clot or gel.

Both coagulase and coagulogen have been extensively studied and characterized. Regarding coagulase, consult Tai et al., "Journal of Biological Chemistry" 252(14): 4773-4776 (1977) and Solum, "Thrombosis Research" 2:55-70 (1973). Coagulogen, and a method for its purification, are described by Gaffin in "Biorheology" 13:273-280 (1976).

The high endotoxin sensitivity of coagulase forms the basis for screening assays for endotoxin pyrogens in human body fluids and biological products. Such assays have been particularly useful in the quality control of pharmaceuticals and parenteral solutions. Several conventional methods exist in which endotoxin is assayed by coagulase-mediated clotting of coagulogen. Included among them are those in which the increase in optical density or viscosity of amebocyte lysate is followed upon mixture with samples thought to contain endotoxin, or in which coagulase activity is assayed by measuring the degree of hydrolysis of a synthetic, chromogenic polypeptide substrate by coagulase.

The widespread adoption of such assays on a commercial scale has been hindered by such unreliable performance, particularly variations in apparent sensitivity to endotoxin encountered among separate lots of Limulus extracts. Such variations have been postulated to be based on seasonal factors, i.e., dependent upon the time of year the Limulus blood is collected. Another theory has been that a component is present in the extracts which affect performance. The component has been characterized as an "inhibitor" of the clotting reaction, reflecting the effect obtained in the presence of the inhibitor. It has been speculated that the inhibitor may be an enzyme [Nachum et al., "Journal of Invertebrate Pathology" 32:51-58 (1978)] or a lipoprotein that simply binds endotoxin [Sullivan et al., "Applied Microbiology" 28(6):1023-1026 (1974)]. Whatever its mode of action, the material will hereinafter be designated as an inhibitor.

It has been suggested to reduce inhibitor activity by combining equal volumes of organic solvent and Limulus lysate, shaking, centrifuging and recovering the aqueous phase (Sullivan et al., op cit). Applicants consider this method to be unsatisfactory because it requires handling toxic or highly flammable reagents and calls for a burdensome phase separation. Furthermore, residual organic solvent may remain in the Sullivan et al. product. Even water-immiscible solvents exhibit a slight solubility in water; in the case of chloroform, this solubility is 0.82 parts per 100 parts of water at 20° C. The effect of this residue on the sample to be assayed may be unpredictable or undesirable.

The presence of the inhibitor in extracts which had been considered "standardized" has prevented the extracts from in fact performing as reliable standards. A standardized extract must produce the same experimental outcome from lot to lot, with only insignificant variation. This is impossible if variable activity of interfering substances in the extracts have not been accounted for. Further, the known "standardized" extracts have not been prepared with suitable consideration of coagulogen concentration. Typical "standardized" Limulus lysates are disclosed in U.S. Pat. Nos. 3,944,391 and 4,038,147. These products have been prepared by simply assaying a lysate batch against a serial dilution of endotoxin to determine the gross potency of the lysate. The principal difficulty with this approach is that it is essentially passive; the extract is in no way treated or processed to yield a single predetermined signal, e.g., development of a given nephelometric endpoint upon reaction with a given endotoxin concentration. This renders quality control more difficult since new standard curves must be prepared at the user level for each new lot of lysate. It is commercially desirable to be able to supply lysate from a variety of lots which will continuously produce the same results in an endotoxin determination using constant endotoxin in concentrations even though the original, untreated lots would have produced a scattering of signals, some higher and some lower than the desired, predetermined level.

Thus it is an object of this invention to produce endotoxin clottable extracts which will yield a reproducible predetermined analytical signal for a given endotoxin concentration within an analytically significant range.

It is an additional object of this invention to replace the previously employed inhibitor inactivation process with one which does not require toxic or hazardous reagents, which is less expensive in both labor and materials and which leaves no potentially interfering residue in the product.

These and other objects of this invention will be apparent from a consideration of this specification as a whole.

SUMMARY OF THE INVENTION

P-nitrophenyl phosphate hydrolase now has been found to be a contaminant of coagulase extracts and an inhibitor in coagulase-based endotoxin assays. Thus, an improved amebocyte extract is prepared by removing p-nitrophenyl phosphate hydrolase from an amebocyte extract which contains inhibitor activity. The resulting extract constitutes a heretofore unappreciated compositions comprising amebocyte coagulase essentially free of p-nitrophenyl phosphate hydrolase activity or containing denatured hydrolase activity. Such improved extracts make possible truly standardized amebocyte lysate compositions comprising amebocyte extracts which are (a) essentially free of p-nitrophenyl phosphate hydrolase activity and (b) contain a predetermined coagulase activity. Optionally, the standardized compositions also contain predetermined concentrations of coagulogen and enzyme cofactors such as metal ions.

Inhibitor activity, including p-nitrophenyl phosphate hydrolase, can be readily removed from amebocyte extracts by a method comprising adjusting the pH of the extract above about 8.5, maintaining the pH until the inhibitor activity is removed and lowering the pH to a level at which coagulase is active.

DETAILED DESCRIPTION OF THE INVENTION

The inhibiting hydrolase was identified by testing extracts containing inhibitor activity against a series of low molecular weight substrates having structures similar to those present in the endotoxin molecule. It was postulated that if an enzyme or enzymes could be found in the extract which act on or competitively bind endotoxin then the inhibition, or lessened apparent coagulase activity, would result from diversion of the endotoxin by a competing enzyme and not from a substance acting on coagulase directly. The ability of inhibitor-containing extracts to hydrolyze the following synthetic chromogenic substrates was determined: p-nitrophenyl phosphate di-tris salt; p-nitrophenyl-2-acetamido-α-D-glucopyranoside; p-nitrophenyl-2-acetamido-B-D-glucopyranoside; p-nitrophenyl-α-D-galactoside; p-nitrophenyl-α-D-glucopyranoside; p-nitrophenyl-B-D-glucopyranoside; p-nitrophenyl-B-D-glucuronide; p-nitrophenyl-α-D-mannopyranoside; p-nitrophenyl laurate; p-nitrophenyl myristate; p-nitrophenyl palmitate; and p-nitrophenyl stearate. Hydrolytic activity in the extract was determined in conventional fashion for each substrate. Only p-nitrophenyl phosphate and p-nitrophenyl-2-acetamido-2-deoxy-B-D-glucopyranoside were hydrolyzed to any significant extent.

When the assays were repeated, except with the addition of varying amounts of endotoxin, only the p-nitrophenyl phosphate hydrolase activity was inhibited by competition from endotoxin. Further, elevating the extract pH as described above removed both hydrolytic activities. Thus it was concluded that the hydrolase present in amebocyte extracts is a competitive inhibitor of the coagulase-endotoxin interaction, and hence of the endotoxin assays.

The endotoxin clottable extract which is the starting material for the improved processes and compositions herein may be any composition containing coagulase. This composition is termed an extract because it is generally obtained by separating the soluble components of Limulus amebocytes from insoluble elements such as cell walls. Nonetheless, it is not essential that the insoluble elements be removed, or even that the cells be lysed if a coagulase assay is employed which is not dependent upon the formation of a clot or suspension of polymerized coagulogen particles. Further, the extract need not contain coagulogen if an analytical substrate other than coagulogen is employed to follow the coagulase activity. It is, however, essential that the starting material contain coagulase.

Once the identity of the agent believed principally responsible for inhibitor activity is known it becomes a matter of routine experimentation to remove its activity from that of coagulase. Removal may be accomplished by (a) inactivating or denaturing the hydrolase in the presence of coagulase without significantly affecting coagulase activity, (b) physically separating the hydrolase from the coagulase or (c) adding a sufficient surplus of a coagulase non-activating hydrolase substrate to the endotoxin assay reaction mixture to competitively inhibit endotoxin-hydrolase interaction. Other methods generally applicable to removing one enzyme activity while leaving another enzyme free to act will be readily apparent to the skilled artisan.

It is not necessary that the inhibitor be entirely removed from the extract. It is generally satisfactory that the extract be substantially free of inhibitor activity, generally no more than about 10% of the original activity in the extract should remain. The degree of removal needed will depend upon the sensitivity for endotoxin which is desired and the variability in inhibitor content within the lots being standardized. Thus, the degree of removal will be a matter of choice.

The hydrolase may be inactivated while leaving coagulase comparatively unaffected by adjusting the pH of the coagulase and inhibitor-containing extract to above about pH 8.5, preferably about 10.8. The discovery that inhibitor activity can be destroyed by a pH adjustment was most surprising. Levin et al. [J. Lab Clin. Med." 75(6):903–911 (1970)] disclose several attempts to remove an inhibitor of the Limulus lysate clotting reaction found in blood plasma. While Levin et al. teach inactivating the inhibitor with chloroform, precipitation with trichloroacetic acid was unsuccessful at removing or inactivating the inhibitor. Parenthetically, the inhibitor in plasma has since been linked to the inhibitor which is found in Limulus extracts (U.S. Pat. No. 4,107,077). Further, not only does Levin et al. suggest that acid is ineffective against the inhibitor, but others have concluded that acidification of lysate irreversibly inactivates coagulase [Solum, "Thrombosis Research" 2:55–70 (1973)]. This is, of course, the opposite result from that which is desired herein. Surprisingly, however, when the pH of the endotoxin clottable extract is raised, rather than lowered, coagulase activity is preserved while the inhibitor is irreversibly inactivated.

A significant advantage of the above described pH shift is that the pH adjustments ordinarily do not result in formation of a precipitate. Thus, unlike the known chloroform procedure it is not necessary to separate any portion of the reaction mixture after inactivation of the inhibitor. A brief centrifugation or crude filtration step may occasionally be desirable if the inhibitor is inactivated at a pH above 11 and the treated extract is to be subsequently used in a nephelometric or optical density method for endotoxin assay. In most circumstances, however, no special treatment of the extract is needed after inactivation of the inhibitor by pH adjustment.

The pH of a typical lysate of Limulus amebocytes is approximately 6.0–7.0. The alkaline pH adjustment of this invention may be made in any conventional fashion, for example by titering an aqueous alkaline solution into the extract with steady stirring. However, crystalline or solid basic substances may be employed in place of solutions. The former is desirable where it is intended to later lyophilize the extract since this technique will not add to the water volume to be removed.

The alkaline material itself may be organic or inorganic, although dilute aqueous solutions of alkali metal hydroxides such as sodium hydroxide are preferred. Alkyl amine is an example of an organic alkaline substance which can be employed. The specific identity of the substance is not critical; it need only raise the pH without causing undesirable side reactions which could inactivate coagulase or coagulogen to a degree which might burden the use of the lysate in an endotoxin assay. It is preferred that a buffer not be included in either the extract or the alkaline substance as this will increase the amount of reagent required to make pH adjustments. Ammonium bicarbonate is particularly useful as an alkalinizing agent because it may be volatilized from the extract, for example by lyophilization, thereby not leaving a salt residue and avoids the need to readjust the pH of the extract to neutrality.

While the alkaline material should exert no deleterious effect on the coagulase, endotoxin or coagulogen, if coagulogen is present it is possible to select a cation which may in fact be of advantage in the assay. For example, manganese or magnesium hydroxide can be employed as at least a portion of the alkaline material since the manganese or magnesium ions also serve as a cofactor for the coagulase. Unfortunately, the use of divalent metal cofactor hydroxides is limited because of their low solubility. In any case a divalent cation cofactor for coagulase should preferably be added to the extract before or concommitant with the alkaline pH adjustment, whether or not the cation-containing composition contributes any alkalinity. The cofactor, however, is not essential.

The extract is incubated at an elevated pH until the desired degree of inhibitor removal has occurred. The degree of inactivation varies with incubation time, temperature and pH. For example, the longer the incubation and the higher the temperature and pH the more rapid is the inactivation. Optimizing these parameters is a matter of routine experimentation for the skilled artisan; the conditions will depend upon the nature of each lot of lysate.

The pH may be adjusted to any point greater than about pH 8.5, generally about from 8.5 to 11 and preferably about pH 10.5 to 11.0. Both coagulase and coagulogen are stable at these hydrogen ion concentrations. However, since other proteins in the extracts may precipitate at a pH of about 11, it may be useful to select a lower pH and incubate for a greater period.

The incubation time sufficient to inactivate the inhibitor will, of course, vary depending upon the amount of inhibitor present and the desired degree of inactivation. Generally, from 20 minutes to 4 hours is sufficient; 90 minutes is preferred at pH 9° and 4° C.

The incubation temperature may range from about 0° C. to the temperature at which coagulase is thermally inactivated; the latter point has been previously determined to be at about 60° C. The temperature should be maintained at about from 0° C. to 40° C., and is preferably held at about 4° C. by immersion of the reaction vessel in an ice bath.

After incubation, the pH should be returned to a level at which coagulase is active. Active coagulase is defined as coagulase capable of reversibly binding endotoxin or coagulase capable of so binding by catalytic action on coagulogen or other suitable substrate. The catalytic alternative is the ordinary measure since it is the basis for present endotoxin assays. The pH readjustment is preferably accomplished by adding an acid using any of the techniques employed to initially raise the pH, although volatilizing ammonium bicarbonate during lyophilization will also perform this function. Generally the pH is readjusted by addition of dilute aqueous acid to the alkaline extract while stirring. A suitable concentration of acid is about 0.1 N. The optimum final pH is one which will yield the optimum sensitivity of the lysate in an endotoxin assay. This is ordinarily coextensive with the optimum pH for coagulase activity, about from pH 6.0 to 7.5 and preferably 7; the lysate is then preferably lyophilized or stored frozen.

The substance used to lower the pH should, like the alkaline substance, not be deleterious to coagulase, or coagulogen if the latter is present. Generally, inorganic acids such as hydrochloric, sulfuric or nitric acid are satisfactory although organic acids may also be employed. The substance may be buffered and in fact, the buffer need not be at an acid pH but may be prepared for use at the final pH desired, e.g. pH 7, and used in an amount sufficient to reduce the pH to that level. Alternatively, a buffer such as tris may be added after the pH has been adjusted to about 7. A divalent cation cofactor for coagulase may also be added to the extract at this time.

The above-described alkalinizing method is the best mode now known to applicants. However, other techniques for removing p-nitrophenol phosphate hydrolase activity from coagulase will be apparent to the skilled artisan. Conventional separation methods such as gel chromatography, ultrafiltration, ion exchange resin chromatography and gel electrophoresis can be used, but such processes employ macromolecular components that should first be made free of endotoxin by extensive washings with water miscible organic solvents such as butanol and pyrogen-free water. Otherwise the endotoxin will contaminate the extracts or, in the case where the extract has not been made free of coagulogen, may clot the extract. While developing suitable washing procedures would be a matter of routine experimentation, it is more economical to employ reagents for the removal which can be readily prepared free of contaminant endotoxin. The pH shift method described above is one example of this. Another method is salting out using crystallizable salts such as ammonium sulfate. Such salts are crystallized, washed free of supernatant, dissolved in aqueous solution and mixed with the amebocyte extract in concentrations sufficient to differentially precipitate coagulase and p-nitrophenyl phosphate hydrolase.

The skilled artisan can determine optimum conditions for salting out by adding the salt to sample aliquots of extract to produce different salt concentrations in each aliquot, e.g., 1, 3, 5, 10, 15 and 20% w/v. The extracts are then centrifuged, the precipitates recovered and redissolved in suitable buffer, and the solutions assayed for coagulase, p-nitrophenyl phosphate hydrolase and, if desired, coagulogen. The salt concentration which yields the maximum coagulase activity and minimum p-nitrophenyl phosphate hydrolase activity is selected for the production run.

The p-nitrophenyl phosphate hydrolase assay is conducted as follows: 2.5 ml of substrate solution (5 mg/ml in tris buffer at pH 7.5) is added to a culture tube, followed by 300 $\mu$l of 50 mM tris buffer pH 7.5 and 200 $\mu$l of test solution. After 30 minutes incubation at 37° C., adsorbence is read at 400 nm on a spectrophotometer, correcting for a blank consisting of 2.5 ml of substrate and 500 $\mu$l of the tris buffer.

The effectiveness of other water soluble, readily-purified reagents can be evaluated in the same fashion. For example, the effect of oxidizing agents such as hypochlorite or sulfhydryl reducing agents can be determined by varying the reaction parameters, e.g., the concentrations of the agents, dilution of the extracts, time of exposure and temperature, then neutralizing any residual agent and determining which aliquot has the maximum coagulase activity and minimum p-nitrophenyl phosphatase activity. The conditions which produce that aliquot will then be employed in the production run.

The coagulase products which are essentially free of p-nitrophenyl phosphate hydrolase activity and which may be prepared following the above procedures are unrecognized in the published literature and are accordingly novel based on the information available to applicants. While an analysis of Limulus extract sold by Mallinckrodt, Inc., has shown no significant hydrolase activity, no evidence is known to applicants which indicates that Mallinckrodt is aware of the unique nature of the extract.

Extracts prepared as described above which are essentially free of inhibitor activity can be standardized against predetermined parameters. In particular, the true coagulase activity now can be assayed and the coagulase activity then adjusted to a predetermined level. It is preferred that the inhibitor be inactivated by the pH adjustment discussed above. However, any other method can be used. Unless the inhibitor activity has been destroyed, the competing reaction kinetics of the inhibitor-endotoxin reaction and the coagulase-endotoxin reaction will make it impossible to standardize the extract over a range of endotoxin concentrations. For example, if the inhibitor-containing extract is assayed for coagulase activity at a coagulase-saturating amount of endotoxin, for example 3 mg/ml, and then filled into containers in an amount such that predetermined enzyme activity will be added to each container (whatever the activity of the original extract lots), the product is found to contain only about 80% of the assayed activity when endotoxin concentrations over the range of 25 to 100 pg/ml are determined. This variance is postulated to be due to diversion of endotoxin by the inhibitor, thus resulting in lower apparent endotoxin levels than are actually present in the original sample. When the endotoxin concentration is so high that all coagulase present is activated, i.e. the coagulase is saturated, diversion of excess endotoxin by inhibitor will not affect the coagulase activity. However if the coagulase is to be used as an indicator of endotoxin concentration, the enzyme a fortiori will not be saturated over the range of endotoxin concentrations expected. In such case the interference by the inhibitor necessarily will be manifested in the endotoxin assay. Similarly, if the extract is standardized at a first, nonsaturating endotoxin level and then assayed at a second level of endotoxin, an extract with inhibitor will yield a different result than one without. This anomalous result is believed to result from the balance of the coagulase and the inhibitor kinetics: At the first endotoxin level, coagulase activation might be favored, while at the second level the action of the inhibitor might be favored.

If the intended assay method is based on coagulogen hydrolysis by coagulase, the standard extract also should contain a predetermined coagulogen concentration which is in such an excess that the assay for endotoxin is not limited by coagulogen over the expected endotoxin range. If coagulase is standardized by simply determining the enzyme activity at one endotoxin concentration and an insufficient quantity of coagulogen is present to indicate true coagulase activity at other more elevated endotoxin levels, the results at such elevated levels will indicate less endotoxin than is actually present. This failing could have a severe adverse impact in the diagnosis of bacteremia or in the quality control screening of parenteral products.

It has been found that coagulogen concentrations are generally proportional to coagulase activity in native Limulus extracts. Thus in many cases it is not necessary to do any more than to confirm that sufficient coagulogen is present; in such cases it would not be necessary to add supplementary coagulogen to the extract. However, it is conceivable that inadvertent exposure of such extracts to extraneous endotoxin during collection and processing might deplete the coagulogen and thereby create a need for coagulogen supplementation. Thus the coagulogen concentration should be determined to be at least a predetermined level or in great excess of a predetermined concentration. The predetermined amount of coagulogen will depend upon the endotoxin concentrations expected in the samples to be assayed. If the samples are expected to be only slightly contaminated, on the order of 1–100 pg/ml, then a coagulogen content in of about 150 $\mu$g/ml lysate will enable the product to be used with most endotoxin-contaminated samples of biological materials. The minimum amount of coagulogen is defined at its lower level by the detection limits of the coagulase assay for endotoxin, and this can be expected to improve as the assay is developed further in the future. On the other hand, the maximum amount to be used is limited only by the maximum solubility of the coagulogen in aqueous solutions; even exceptionally high endotoxin concentrations, for example 1.0 mg/ml, could be theoretically determined by coagulogen hydrolysis-product formation, particularly where the product is removed from the reaction mixture as the hydrolysis proceeds. Since a coagulogen content of over 100–400 $\mu$g/ml will not adversely affect the assay and the lower coagulogen concentration is defined by the state of the art in detecting coagulogen hydrolysis products, the selection of a particular predetermined coagulogen content is presently a matter of choice.

Coagulogen may be determined by modifying the Munford assay for endotoxin disclosed in "Analytical Biochemistry" 91:509–515 (1978). Instead of assaying unknown endotoxin, as provided in that method, a fixed endotoxin concentration is used with $^{125}$I-labelled coagulogen, unknown coagulogen and coagulase. Following an incubation period, the clot-bound radioactivity is determined as in a typical competitive-type radioimmunoassay. A large quantity of coagulogen will displace labelled coagulogen from coagulase-mediated precipitation, and vice versa with comparatively lower levels of coagulogen. Thus, the greater the clot-bound radioactivity the lower is the coagulogen concentration. The method is quantifiable by use of purified coagulogen standards.

If the coagulogen concentration is lower than the predetermined level it will be necessary to increase the coagulogen level in the extract. For example, a coagulogen-rich extract or purified coagulogen may be mixed with the extract to achieve the desired increase in coagulogen concentration. Alternatively, the coagulogen may be concentrated by ultrafiltration.

In preparing a standardized, endotoxin clottable extract it is necessary to determine the coagulase activity. This may be accomplished by any of the known coagulase assay methods; these methods frequently have been used to determine endotoxin concentration as well. Here, however, a known, preferably saturating concentration of endotoxin is used. A saturating endotoxin concentration is generally in excess of about 1 mg/ml endotoxin, preferably 3 mg/ml. The assay results may be converted into arbitrary enzyme units since for standardization purposes it is the relative rather than absolute enzyme activity which is relevant. Once the coagulase activity of the extract has been determined the extract is proportioned into an endotoxin assay reaction mixture in an amount calculated to produce the selected enzyme activity. For example, the treated extract may be added directly to the endotoxin assay reaction mixture in a volume calculated to yield the predetermined activity. Since it is more expeditious for the analyst to always add a fixed volume of extract, containers for storing the extract can be filled with an amount of extract calculated to contribute the predetermined activity upon reconstitution in a constant amount of aqueous solution; a proportional fill relieves the user of the burden of proportional reconstitution. The extract may then be lyophilized.

The invention will be more fully understood by reference to the following examples.

EXAMPLE I

Two lots of *Limulus polyphemus* amebocytes were separately collected and lysed by the method of United Kingdom Pat. No. 1,499,846. One lot was designated a reference lysate. The remaining lot was employed as the starting material in the preparation of standardized lysate in accordance with the method of this invention. It was designated lot 8-113.

Both lots were first assayed for coagulase activity. 50 mM Tris buffer at pH 7.5 and containing 10 mM $MgCl_2$ was used wherever buffer is mentioned below. *E. coli* endotoxin (055:B5, Difco Laboratories) was dissolved in buffer. Coagulogen was prepared in a concentration of 8.0 mg/ml in buffer by the method of Solum, supra, except that the crude lysate was precipitated with ammonium sulfate at 80% of saturation before redissolution and placement on the Sephadex column, the column then eluted with phosphate buffer and the eluate further purified on a carboxymethyl cellulose column. 0.1 ml of a 3.0 mg/ml endotoxin solution, 0.1 ml of coagulogen solution, 0.1 ml of lysate and 2.7 ml of buffer were mixed and incubated for 8 minutes. After incubation the change in optical density at 360 nM and 37° C. was recorded. One enzyme unit was arbitrarily defined as a 0.001 absorbance unit change in optical density at 360 nM. The reference lot and lot 8-113 exhibited an enzyme activity of 665 and 440 units/ml, respectively.

Since the plot of optical density against lysate fill volume (or dilution) is not a straight line, the quantity of reference and 8-113 lysate which will yield the same coagulase activity will not be directly proportional to the arbitrarily assigned optical density units described above. Because of this dilution effect the amount of 8-113 lysate needed to produce the same activity as the reference lysate is readily calculated from the above described plot as only 2.65 ml. Thus 2 ml and 2.65 ml of reference and 8-113 lysate, repsectively, were added to the containers. The vial contents were then lyophilized.

Next the inhibitor activity of the lots was inactivated by the novel method of this invention. Two vials of the reference lysate and two vials of lysate to be standardized were reconstituted in 2.5 ml of sterile $H_2O$. One vial of each lot was adjusted to pH 9.0 with 0.1 N NaOH and incubated at 4° C. for 90 minutes. Then the pH in each vial was reduced to 7.5 by stirring in 0.1 N HCl at 4° C. 2.5 ml of buffer was added to each vial and the lysate assayed against the above *E. coli* endotoxin at endotoxin concentrations of 0, 25, 50 and 100 pg/ml.

The assay method was essentially that shown in United Kingdom Pat. No. 1,499,846. Table I below compares the optical density at 650 nM of the treated and control lysates.

TABLE I

| Endotoxin Concentration | Lysate With Coagulase and pH Adjustment | | Control Lysate | |
|---|---|---|---|---|
| pg/ml | Reference | 8-113 | Reference | 8-113 |
| 100 | 0.826 | 0.812 | 0.683 | 0.562 |
| 50 | 0.577 | 0.565 | 0.486 | 0.359 |
| 25 | 0.362 | 0.361 | 0.285 | 0.207 |
| 0 | 0.161 | 0.124 | 0.135 | 0.112 |

As can be seen by these results, the alkaline treatment in conjunction with the proportional distribution of coagulase both increased the sensitivity of the lysates to endotoxin and eliminated the variability encountered with native lysate. With the pH adjustment, the standard lot continued to exhibit coagulase activity approximately equal to that of the reference, in the order of from 97.9 to 99.7% of the reference activity, while without the adjustment the 8-113 lot contained an apparent activity at 25, 50 and 100 pg/endotoxin/ml, respectively, of only 72.6%, 73.9%, and 82.3% of the reference lot activity.

EXAMPLE II

The procedure of Example I was repeated with reference lot and another lot of lysate, designated 8-112. As in Example I with lot 8-113, the coagulase activity of lot 8-112 had been proportioned to the same level as the reference lot. However, in this example the inhibitor was inactivated by a chloroform extraction. Chloroform was thoroughly mixed with the reference lot and lot 8-112 in a 1:2 proportion of chloroform to lysate, and incubated at 4° C. for 60 minutes. The lysate-chloroform mixtures were centrifuged to remove precipitate and undissolved chloroform and afterwards treated and assayed in the same fashion as in Example I. The results are tabulated below.

TABLE II

| Endotoxin Concentration | Lysate With Chloroform Extraction | | Control Lysate (No Extraction) | |
|---|---|---|---|---|
| pg/ml | Reference | 8-112 | Reference | 8-112 |
| 100 | 1.224 | 1.400 | 1.044 | 0.773 |
| 50 | 1.008 | 1.111 | 0.695 | 0.528 |
| 25 | 0.774 | 0.717 | 0.469 | 0.391 |
| 0 | 0.214 | 0.165 | 0.195 | 0.170 |

The chloroform extraction technique resulted in a lysate showing greater variation among assays at various endotoxin concentrations than encountered with the pH adjustment method of Example I, i.e., lot 8-112 was 14.4% and 10.2% more active than the reference lot and 7.3% less active at, respectively, 100, 50 and 25 pg/ml of endotoxin. Interestingly, Limulus extract sold by Associates of Cape Cod, which is believed made by a chloroform extraction method, contains significant p-nitrophenyl phosphate hydrolase activity.

We claim:

1. A method for inactivating inhibitor in coagulase-containing amebocyte extracts which comprises adjusting the pH of the extract above about 8.5 to inactivate the inhibitor, followed by lowering the pH to a level at which coagulase is active.

2. A method for inactivating inhibitor in coagulase-containing amebocyte extracts which comprises increasing the pH of the extract until the desired degree of inactivation has occurred and then lowering the lysate pH to about 7.

3. A method comprising removing p-nitrophenyl phosphate hydrolase activity from coagulase-containing amebocyte extracts by increasing the pH of the extract until the desired degree of inactivation has occurred and then lowering the lysate pH to a level at which coagulase is active.

4. The method of claim 3 wherein the hydrolase is denatured by adjusting the pH of the extract above about 8.5, followed by lowering the pH to a level at which coagulase is active.

5. A method for preparing a standardized amebocyte extract from inhibitor- and coagulase-containing amebocyte extract which comprises:
(a) adjusting the pH of the extract above about 8.5 to inactivate the inhibitor, followed by lowering the pH to a level at which coagulase is active;
(b) determining the coagulase activity of the extract;
(c) determining the coagulogen content of the extract and, if the coagulogen content is not in excess of a predetermined level, adjusting said content so that it is in excess of said level.

6. The method of claim 5 wherein the coagulogen content is adjusted by adding coagulogen.

7. The method of claim 5 wherein the extract is separated into portions by dispensing volumes of extract into containers so that each container holds a predetermined coagulase activity.

8. The method of claim 7 wherein the extract is lyophilized after being dispensed into the containers.

* * * * *